United States Patent [19]

Frei et al.

[11] 4,250,894
[45] Feb. 17, 1981

[54] INSTRUMENT FOR VISCOELASTIC MEASUREMENT

[75] Inventors: Ephraim H. Frei; Bruce D. Sollish; Shmuel Yerushalmi, all of Rehovot; Sidney B. Lang, Beer-Sheva; Mordechai Moshitzky, Rehovot, all of Israel

[73] Assignee: Yeda Research & Development Co., Ltd., Rehovot, Israel

[21] Appl. No.: 960,591

[22] Filed: Nov. 14, 1978

[51] Int. Cl.³ .............................................. A61B 10/00
[52] U.S. Cl. ..................................... 128/774; 73/626; 128/630
[58] Field of Search ............... 128/774, 780, 782, 630; 73/78, 626, 629

[56] References Cited

U.S. PATENT DOCUMENTS

| | | | |
|---|---|---|---|
| 3,308,476 | 3/1967 | Kleesattel | 73/78 |
| 3,323,352 | 6/1967 | Branson | 73/78 |
| 3,744,490 | 7/1973 | Fernandez | 128/2.05 |
| 3,880,145 | 4/1975 | Blick | 128/2.05 |
| 3,970,862 | 7/1976 | Edelman et al. | 128/2.05 |
| 3,972,227 | 8/1976 | Tomilov | 73/629 |
| 4,023,562 | 5/1977 | Hynecek et al. | 128/2.05 |
| 4,144,877 | 3/1979 | Frei et al. | 128/774 |
| 4,159,640 | 7/1979 | Leveque et al. | 128/774 |

OTHER PUBLICATIONS

37 Transducer for the Continuous External Measurement of Arterial Blood Pressure", Pressman and Newgard, IEEE Transactions on Bio Medical Electronics, Apr. 1963, pp. 73-81.

Primary Examiner—Robert W. Michell
Assistant Examiner—C. W. Shedd
Attorney, Agent, or Firm—Ostrolenk, Faber, Gerb & Soffen

[57] ABSTRACT

An instrument for viscoelastic measurement, particularly for breast palpation, uses a plurality of spaced elongated electret strips which are pressed into the body being examined by a pressure member which applies a given periodic or steady stress to the tissue beneath the electret strips. Electronic measuring means then interrogates the output voltage of each of the strips in turn and the output of each strip is displayed to produce a display characteristic which will show the presence of an inclusion in the breast tissue being examined.

8 Claims, 12 Drawing Figures

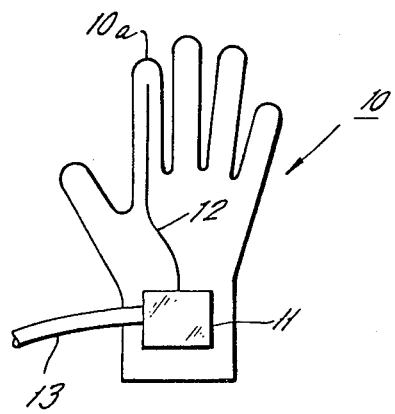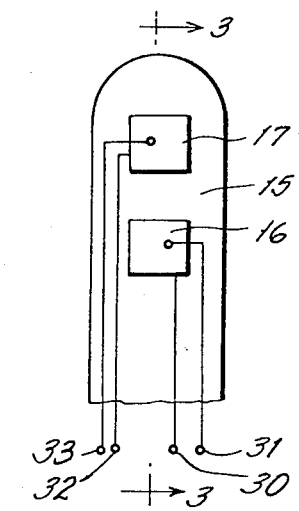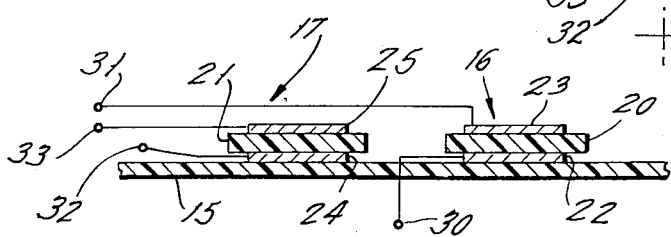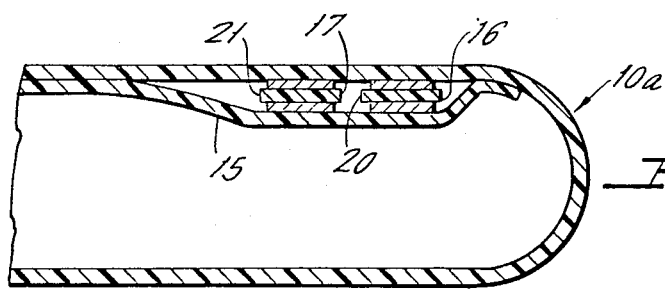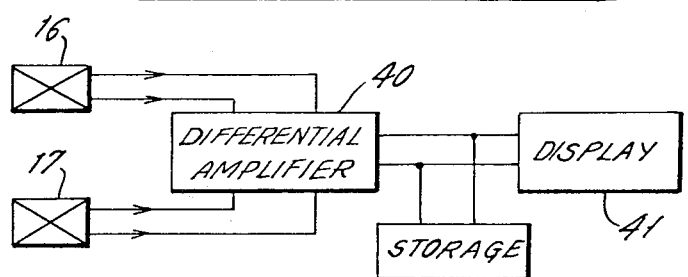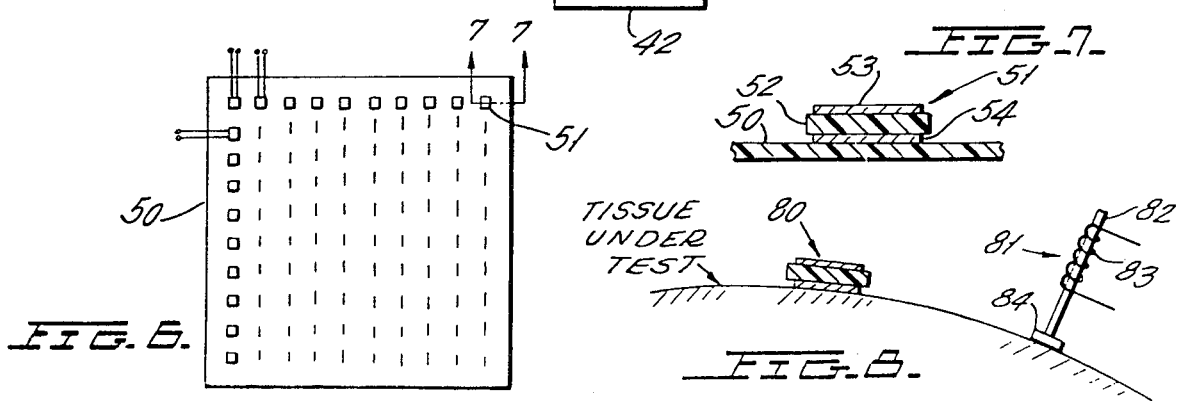

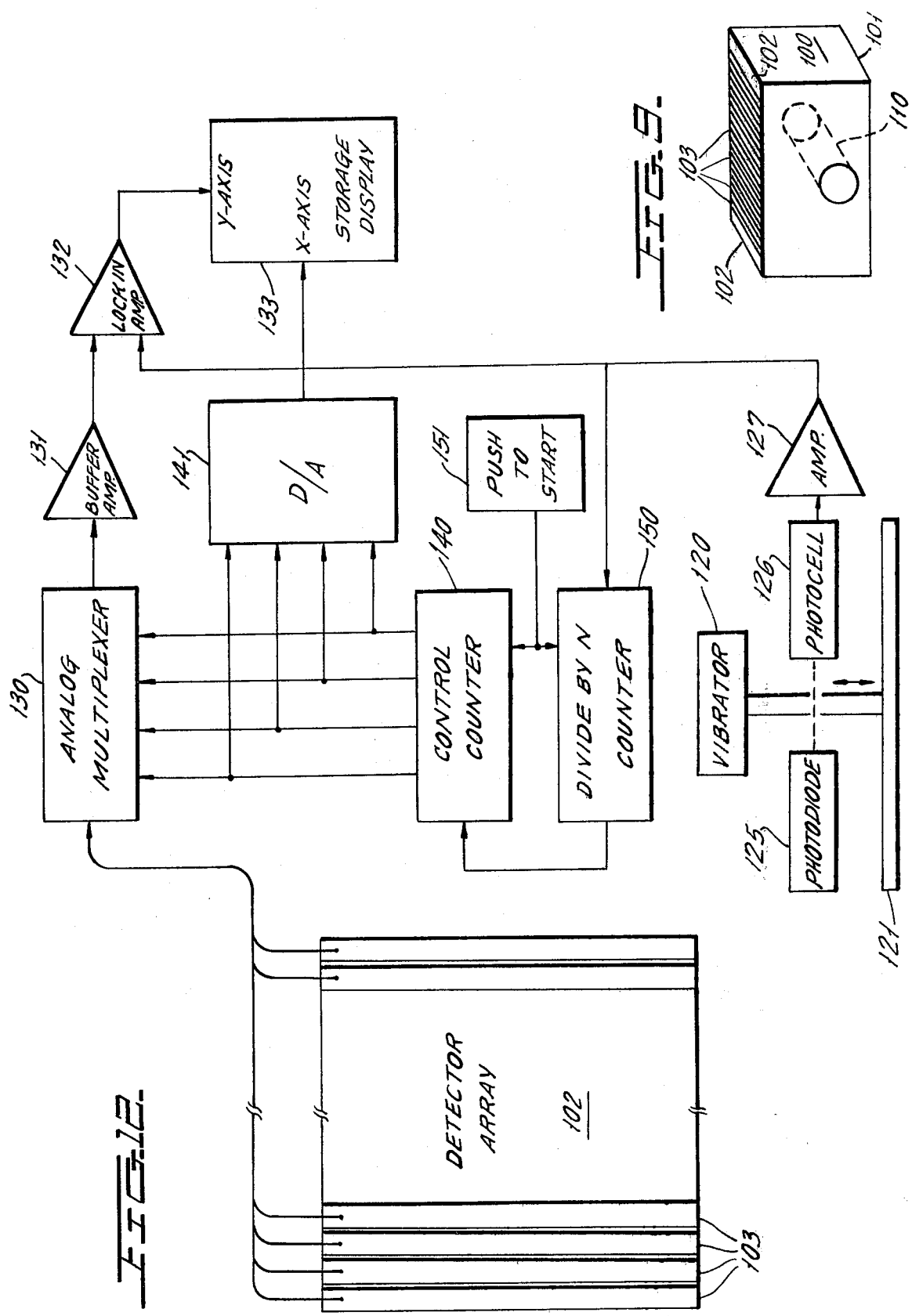

INSTRUMENT FOR VISCOELASTIC MEASUREMENT

BACKGROUND OF THE INVENTION

This application is an improvement of copending application Ser. No. 713,891, filed Aug. 12, 1976 (W-146), now U.S. Pat. No. 4,144,877. This invention relates to an apparatus and method for viscoelastic measurement to discover thickened regions in human tissue, and more specifically relates to a novel transducer head with at least two spaced transducer elements of small area to enable improved examination of human tissue, particularly breast tissue, whereby very small thickened regions can be discovered, and whereby the palpation procedure can be done more quickly than at present, and can be carried out with relatively little training of the examiner.

Three main methods are at present used for the diagnosis of breast cancer: X-ray-mammography, thermography and palpation. Some work is also being done with ultrasonic waves. None of these methods is adequate alone, nor is a combination of several of them satisfactory. Palpation, in general, is not able to detect tumors of less than about one centimeter in size.

One of the most accurate methods in use is palpation, but this is done manually, is subjective, is time-consuming, and is costly. No instrument has so far been developed to carry out the palpation method. This is mainly due to the fact that no well working transducer can transform the information related to the tactile sense into electronic signals in the range of the consistencies (mechanical impedance) of living tissue.

The present invention provides a novel instrument to obtain the same information as a physician obtains through palpation, which instrument can analyze viscoelastic properties better, which can permit the recording of the information and which provides an objective, rapid, and reliable method to diagnose pathological states especially breast cancer.

BRIEF DESCRIPTION OF THE INVENTION

In the invention previously disclosed in parent application Ser. No. 713,891 (W-146), a plurality of small piezoelectric elements, which are spaced from one another, are arranged in a suitable array. The transducer elements may be in the form of spaced fingers one to five millimeters wide and spaced by one to five millimeters. The fingers can be laterally spaced from one another, or a plurality of fingers can surround a central finger, or any other array can be used. The transducer elements are then suitably secured relative to one another, for example at the fingertip of a flexible glove. Thus, the user's finger can press the transducer elements into a local tissue area, applying about the same pressure to each transducer element, and each transducer element will develop an output related to the consistency of the tissue beneath the individual transducer element. A difference in the output of one transducer element from that of an adjacent transducer element can then identify the border of the body of a thickened tissue region of very small diameter, much smaller than the least diameter lump which a skilled physician might detect when manually palpating a patient.

This information regarding the consistency of the tissue beneath each transducer element may be presented on an X-Y recorder to record the position of the transducer at each position, and also record the value of the stress encountered at that position. This could be done with present commercially available X-Y recorders, by vibrating the pen of this recorder, so-called "Z" presentation. A storage oscilloscope could also be used. As the stress in normal cases will change appreciably from location to location when scanning the breast, it may be desirable to record nonlinearity of the stress-strain dependence to show better significant changes in consistency of the underlying tissue.

In order to speed up the procedure, several transducer heads can be simultaneously operated. Thus, there may be several pens recording in parallel on the X-Y recorder, or several traces recording in parallel on the storage oscilloscope. It is also possible to record the difference of the signal of two adjacent transducers.

Any desired transducer material can be used for the elements, such as piezoelectric ceramic transducers, differential transformers, pliable resistors which change resistance with pressure and piezoelectric electret transducers. Electrets are made of organic compounds typically formed by cooling from liquid or soft state to the solid state in the presence of an electric field or by polymerization in the presence of an electric field. Conducting electrodes are deposited by known means. Typical materials used to make electrets are beeswax and polymers such as polyvinylidene fluoride. The electrodes can be in individual or array configuration. Such electrets are useful as the transducer elements since their mechanical impedance is well matched to the impedance of living tissue. Moreover, the consistency of an electret can be widely changed by using different substances or different combinations of substances. The matching of the impedance of the transducer to the tissue being examined has the advantage of higher sensitivity, better signal-to-noise ratio, and more comfort during the test.

As described before, the transducer itself exerts a stress on tissue and the strain resulting from this stress is measured. But palpation with such a transducer can also be done by inducing a variable strain with another, and active element, on a nearby location of the tissue. The strain and stress resulting will be transmitted through the tissue and will give a signal at the transducer. To give a very simple example, a small hard part of the tissue is moved by the straining element below the transducer. In such a case, the transducer will indicate a higher strain when the hard tissue passes below it.

If desired, the signal produced by the transducer head can be processed through a computer which also can control the positions of the transducer or transducers. This computer could go into different modes, for instance to scan in detail any suspect area.

The instrument of the invention can be advantageously used for:

(a) Screening a large number of patients with the help of a technician only and print a record of the procedure.

(b) The novel transducer can measure fine differences of consistency to get better differentiation of different pathologies.

(c) A transducer element can be smaller than a human finger. Thus, it can detect tumors of a smaller size than is possible at present with palpation.

In accordance with the present improvement, the transducer head consists of a plurality of parallel spaced electret strips fixed to a flexible mounting sheet. A pressure applying vibrator then applies a low frequency stress over the full surface of the electret sheet to apply a low frequency (or periodic) stress, superimposed on a d-c (or steady) stress or pressure. In some cases, a high steady stress only may be applied to the electret sheet. In addition, the breast may be stressed either by mechanical means to produce non-linear normal or shear stresses. The electret may either respond to the non-linear viscoelastic strains known as "negative dilatancy" or to other non-linear effects. The output of each electret strip is then interrogated by a suitable electronic monitoring system, and the output voltages of the strips are presented in a Cartesian coordinate display. The shape of the display will reveal the presence of a lump or hardened region in the breast tissue underlying the transducer head.

BRIEF DESCRIPTION OF THE DRAWINGS

FIG. 1 is a top plan view of a glove which is equipped with the transducer head of the present invention and which contains a lead connector on the back of the glove which is provided with an output conductor which leads to appropriate processing circuits.

FIG. 2 is an enlarged view of a transducer head insert which is to be fixed inside the front tip of the forefinger of the glove of FIG. 1 with the transducer elements facing outwardly of the glove.

FIG. 3 is a cross-sectional view of FIG. 2 taken across the section line 3—3 in FIG. 2.

FIG. 4 is an enlarged cross-sectional view of the forefinger of the glove of FIG. 1 illustrating the transducer head assembly of FIGS. 2 and 3 affixed therein.

FIG. 5 is a block diagram illustrating one processing circuit arrangement which could be used in connection with the transducer arrangement of FIGS. 2, 3 and 4.

FIG. 6 is a plan view of the embodiment of the invention in which a large number of transducer arrangements are arranged in an array.

FIG. 7 is a cross-sectional view of FIG. 6 taken across the section line 7—7 in FIG. 6.

FIG. 8 is a side view illustrating the arrangement of the special element exerting stress.

FIG. 9 schematically shows a model used for the mathematical calculation of stresses produced in a sheet of electret strips in accordance with the improvement of this invention.

FIG. 12 is a circuit diagram showing the preferred embodiment of the present invention.

DETAILED DESCRIPTION OF THE DRAWINGS

Figure 10:
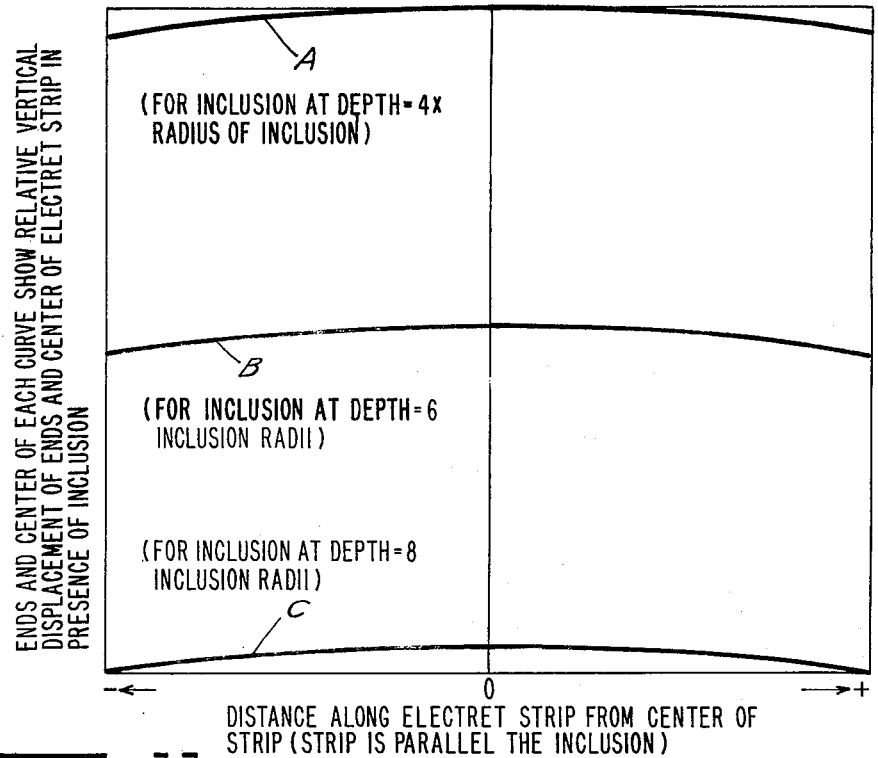
FIG. 10 shows three plots of output voltage along the length of one of the electret strips of FIG. 9 for inclusions of three depths respectively beneath the center of the strip.

The following description of FIGS. 1 to 8 is taken directly from co-pending application Ser. No. 713,891 (W-146), now U.S. Pat. No. 4,144,877. Referring first to FIG. 1, there is illustrated a plan view of the back of a flexible glove 10 which has an electrical connector 11 secured to the back thereof. The electrical connector receives an input cable 12 coming from a transducer head (not visible in FIG. 1) which lies along the front side extending from the tip of the forefinger. Connector 11 also has an output conduit 13 leading from glove 10 to appropriate processing circuits. The construction of glove 10 may be of the form of the conventional surgeon's glove and at least the glove portion receiving the transducer head will be extremely thin so as to not interfere with the application of uniform pressure between the transducer head and the tissue which is to be palpated.

FIGS. 2 and 3 illustrate one example of a transducer head construction which can be fitted into the forefinger of the glove of FIG. 1. In FIGS. 2 and 3, the transducer head insert consists of a thin, flexible rubber membrane support 15 which has cemented thereto a pair of spaced transducer elements 16 and 17. While the transducers 16 and 17 may be of any desired type, they are preferably formed of a type which is matched to the impedance of human tissue.

One commercially available piezoelectric transducer material which has been used in connection with the present invention, known by the trademark "Dynacon", is a rubber material impregnated with a conductive material and which exhibits good piezoelectric properties at relatively low pressures. Electrets are also useful as the transducer elements of the invention since they have an impedance which is fairly well matched to the impedance of human tissue.

The transducer elements 16 and 17 consist of a central transducer layer of the electret of rubber or other materials 20 and 21, respectively, and electrodes are painted or deposited on the opposite surfaces of the piezoelectric bodies shown as electrodes 22 and 23 on body 20 and electrodes 24 and 25 on body 21. Electrodes 22, 23, 24 and 25 are then connected to suitable leads which are schematically connected in FIGS. 2 and 3 as the leads terminating with terminals 30, 31, 32 and 33. While lead 30 is schematically illustrated for clarity in FIG. 3 as penetrating the support membrane 15, in fact all leads may be cemented to the top of the membrane 15.

Each of the two transducer elements 16 and 17 of FIGS. 2, 3 and 4 are relatively small in size and typically may be about five millimeters by five millimeters in area and from about five micrometers to one millimeter in thickness. The transducer elements can have any desired surface shape other than the square shape illustrated.

The entire assembly of FIGS. 2 and 3 may then be cemented into the front fingertip 10a of the glove 10 of FIG. 1, as shown in FIG. 4. Thus, the upper surface of the transducers is covered by the thin membrane of glove fingertip 10a which, however, is made sufficiently thin so as to not interfere with the transfer of energy from the transducer elements 16 and 17 to the tissue being palpated beneath the fingertip 10a.

The transducer members 16 and 17 are also spaced from one another by about five millimeters' spacing between their adjacent parallel edges. The spacing chosen can be less than five millimeters, and will be related to the geometry of the particular transducer element. The transducer elements 16 and 17 are so positioned within fingertip 10a that the user of the glove has the transducer elements located near the center of his fingertip so that the two transducer heads 16 and 17 can be pressed against tissue being palpated in a manner which closely resembles the manual palpation technique.

The closely spaced transducer elements 16 and 17, however, will produce different outputs if they are pressed against tissue region containing some small thickened area beneath or partly beneath one transducer but not the other. Thus, an extremely sensitive output is produced from the transducer head arrangement which could not be produced by manual palpation since the palpation method can seldom sense thickened regions less than about one centimeter in diameter.

FIG. 5 illustrates one circuit diagram for processing the output signals of the piezoelectric transducers 16 and 17. Thus, in use, the transducers 16 and 17 of FIG. 5 are each pressed against human tissue, such as breast tissue, and output signals are produced from the transducers 16 and 17 which are related to the viscoelastic properties of the tissue being strained. These output signals are then applied to a differential amplifier 40 which will measure a difference between the two output signals which would be indicative of a difference in the viscoelastic properties of the tissue beneath transducers 16 and 17. The differential amplifier output may then be connected to a suitable display 41. At the same time, the output signals from differential amplifier 40 may be connected to a suitable storage medium 42, whereby the output signals can be stored and later processed in any desired manner as by computer processing for display in a recorder, which display would be coordinated with the X-Y coordinates of the transducer head arrangement. For this purpose, the transducer head arrangement of FIG. 2 can be connected to an X-Y coordinate generator of any well-known variety.

In the example of FIGS. 2, 3 and 4, the transducer head construction used only two transducer elements 16 and 17 which were spaced from one another. It should be understood that the present invention contemplates the use of any number of transducer elements arranged relative to one another in any pattern and the use of the two spaced transducer elements simply illustrates the basic concept of the invention. It should further be noted that the transducer elements may be dimensioned smaller than the illustrative five millimeters by five millimeters and may have closer spacings than disclosed in order to increase the sensitivity of the device.

It is not necessary to arrange the transducer head in the finger of a glove and, if desired, a transducer matrix can be arranged on a flexible membrane which could, for example, contain an array of one hundred transducer elements in a ten centimeter by ten centimeter area, with the elements being arranged in orthogonal rows and lines. This array may then be used for breast palpation by placing the array against the breast and then having the patient lie flat against a plate which will apply a pressure over the entire array, with the individual transducers of the array producing electric outputs related to the tissue viscoelastic properties immediately beneath the individual transducer element. The output signal of each transducer element may then be read out in a multiplex fashion to produce a suitable display and processed to determine differences between the outputs from adjacent tissue regions.

An array such as the one described above is illustrated in FIGS. 6 and 7, wherein the array is mounted on a thin, flexible rubber membrane 15 which can have a thickness, for example, of one millimeter and wherein the array consists of ten rows of ten transducers arranged in ten columns orthogonal to the rows.

A typical transducer 51 of the array is shown in FIG. 7 as consisting of a transducer body 52 which consists of a rubber material impregnated with conductive material of the type known by the trademark "Dynacon", with painted electrodes 53 and 54 formed on the opposite surfaces of the transducer body 52. The transducer body 52 is then cemented to the flexible sheet 50.

Leads attached to the electrodes 53 and 54 then extend from the electrodes of each of the transducers and into a suitable cable (not shown). Some of these leads are schematically shown in the upper lefthand corner of FIG. 6.

In the embodiments of FIGS. 6 and 7, the sheet 50 may be a sheet having a dimension of about ten centimeters by ten centimeters, with the individual transducer elements having a dimension of about five millimeters by five millimeters, the transducers being spaced from one another by about five millimeters.

FIG. 8 shows a further embodiment of the invention wherein a passive transducer 80, having the structure of FIG. 7, is spaced from five millimeters to several centimeters from head 81 applying a shear stress, which caused a shear strain in the tissue. Shear applying head 81 consists of a magnetic armature 82 surrounded by a solenoid 83 which is connected to a suitable electrical energizing source (not shown). A small rubber application pad 84 is connected to the bottom of armature 82. In addition, pulses applied to solenoid 83 cause stress to be applied to the tissue beneath applicator 84, with attendent stresses applied to passive transducer 80, depending upon the viscoelastic properties of the tissue between pad 84 and transducer 80.

The improvement of this invention can be understood from the schematic and mathematical model of FIG. 9. Referring to FIG. 9, a mass of breast tissue 100 is shown bounded by a rigid bottom plane 101 and its upper surface is bounded by a flexible sheet 102 which carries a plurality of spaced, elongated electret strips 103. By way of example, the sheet 102 may be a sheet of stretched and poled polyvinylidene fluoride having a thickness of about 9 micrometers with a plurality of electret strips 103. By way of example, 16 strips 103 can be provided which are each 2 millimeters wide and spaced from one another by 2 millimeters. The overall detection array is 62 millimeters by 62 millimeters. Other electret materials, and other dimensions could be used.

The model of FIG. 9 illustrates a cylindrical inclusion 110, which is a thickened volume embedded in the mass 100 of softer breast tissue, and is parallel to the plane of the strips 103.

In accordance with the invention, a uniform compressive stress is imposed upon the electret sheet 102. The stress can be either steady or periodic provided that the frequency is below the resonance frequency of the electret sheet (on the order of several megahertz). The stress produces an elastic strain at every point in the model. The electret strips 103 convert the strains at their respective locations into electric voltages which give information of both the size and the depth of the inclusion.

It is assumed that the elastic strains in the model of FIG. 9 are two-dimensional ("plane strain") and that they are infinitesimally small. Both the softer material 100 and the inclusion 110 are assumed to be elastically isotropic and each is characterized by a single modulus of elasticity and a Poisson's ratio. These assumptions are not critical and relaxation of them produces similar results. The elastic displacements for this geometry in polar coordinates using the cylinder axis as the origin are shown by J. N. Goodier, "Concentrations of stress around spherical and cylindrical inclusions and flaws", J. Appl. Mech. 55, 39 (1933). In the analysis following in FIGS. 10 and 11, the coordinates are transformed to a Cartesian system, and the displacements and strains in both the horizontal and vertical directions at the electret sheet 102 are calculated.

Typical polymer electret materials have a piezoelectric tensor corresponding to the crystallographic point group mm2. In these materials, a voltage is produced between the upper and lower surfaces of the sheet in response to tensile strains in the plane of the sheet and compressive strains normal to it. The voltages generated by the strain produced in the model arrangement of FIG. 9 were calculated using the piezoelectric equations published by W. P. Mason, "Crystal Physics of Interaction Processes" (Academic Press, New York, 1966), Chapter 4. Experimental values of the piezoelectric coefficients measured on polyvinylidene fluoride by J. Ohigashi, "Electromechanical properties of polarized polyvinylidene fluoride films as studied by the piezoelectric resonance technique", J. Appl. Phys. 47, 949 (1976) were used.

Figure 11:
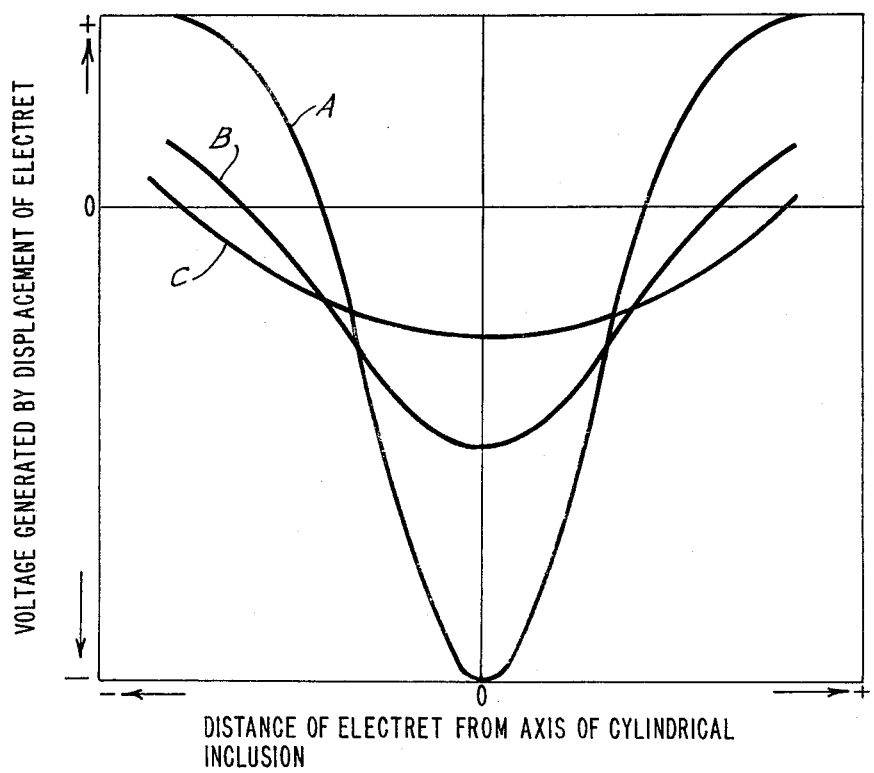
FIG. 11 shows three plots of output voltage of the different electret strips which are laterally displaced from the center line of an inclusion for three inclusions respectively which are at different depths.

A calculation was then made of the elastic displacements at the electret film and the corresponding piezoelectric voltages. FIG. 10 shows the vertical displacement and FIG. 11 shows the output voltage along the length of electret strips 103 and perpendicular thereto for a given inclusion diameter, different depths of the inclusion, a given applied compressive force, a given thickness of the electret sheet, a given elastic modulus of both the softer material and the inclusion, a given Poisson's ratio of both the softer material and the inclusion, and the relevant piezoelectric moduli of the electret films.

Values of the parameters used in the calculations are given below. These values are typical ones, used only for illustration.

Inclusion diameters = 0.5 cm.
Ratio of applied compressive force to elastic modulus of softer material = 0.01.
Ratio of elastic modulus of inclusion to that of softer material = 4.
Poisson's ratio of softer material = 0.3.
Poisson's ratio of inclusion = 0.3.
Thickness of electret sheet = 100 $\mu$m.
Width of the electret strips = 1 cm.
Piezoelectric moduli of electret: $d_{31} = 0.110$ c/m$^2$, $d_{32} = 0.02$ c/m$^2$, $d_{33} = -0.165$ c/m$^2$
Dielectric constant of electret = 7.7.

In each figure, Curve A represents values calculated in a plane which is 4 inclusion radii above the inclusion; Curve B in a plane 6 inclusion radii above the uppermost surface of the inclusion; and Curve C in a plane 8 inclusion radii above the inclusion. FIG. 10 shows the vertical displacement of each point on the electret sheet 102 as a function of its distance from the line bisecting the electrets. Note that displacements are greater as the thickness of material between the inclusion and the polymer sheet increases.

FIG. 11 shows the predicted piezoelectric voltage for electret strips 103 as a function of their lateral position from the center of sheet 102. There is a relatively large voltage output, even for deeply embedded inclusions. In every case, the sign of the piezoelectric voltage changes from negative to positive as the strip location is moved farther from the center line of member 102. A combination of the piezoelectric voltage when the electret strip is over the inclusion and the locations of the zero piezoelectric voltages are sufficient to permit determinations of both the size and depth of an inclusion.

Even though the behavior of living biological tissues would be expected to give a much more complex piezoelectric "picture", the analysis of the size and location of thickened areas would be quite similar. Therefore, the above analysis illustrates the basic features of the invention.

A straightforward extension of the above description would apply to a three-dimensional strain analysis in which there are one vertical and two horizontal strain components. In this case, a two-dimensional array of detector elements is required. The basic principles of the analysis remain valid, namely, vertical displacement is a minimum at the element directly over the inclusion, and the piezoelectric voltage changes sign in the vicinity of the inclusion.

Additional modes of analysis are made possible by stressing the breast manually or mechanically while piezoelectric measurements are being made. The stress may be normal or shear, static or periodic, or combinations of any of these. The stresses may excite non-linear second order effects, such as contraction perpendicular to the shear plane.

A particular embodiment of the invention suitable for use with the above model is shown schematically in FIG. 12. In FIG. 12, the piezoelectric detector 102 (typically of stretched and poled polyvinylidene fluoride, 9 micrometers thickness, manufactured by Kureha) is formed into an array of adjacent strip elements 103 by selective etching of the electrode surface. The implementation shown consists of sixteen 2 millimeters wide strips, with separation between strips of 2 millimeters. The overall size of the detector array is 62 millimeters by 62 millimeters.

A source of cyclic stress of frequency such as mechanical vibrator 120 is coupled to a pressure plate 121 which covers the surface of array 102 and applies stress through the transducer array 102 to the body under investigation. Typically, the vibrating frequency is thirty hertz.

The vibrator frequency is measured by a coupled light source 125, which may be a photodiode, photocell 126 and amplifier 127. The light source is interrupted by vibrations of the shaft connecting vibrator 120 and pressure plate 121. Thus, the output of photocell 126 and amplifer 127 is a periodic time function synchronized to the vibrator 120. The output of amplifier 127 is the reference signal for the device.

The output of each of the individual strips 103 is connected to the analog multiplexer 130, the output of which is connected to buffer amplifier 131 and to one input of lock-in amplifier 132. The output of amplifier 127 is connected to the reference input of amplifier 132. The output of amplifier 132 is then connected to the Y-axis deflection input of a suitable storage display 133, and will produce a Y-axis deflection related to the output voltage of the electret strip which has been selected by the multiplexer 130.

A suitable control counter 140 is then connected to control the multiplexer 130 and the activated channel is connected through the D/A converter 141 which in turn is connected to the X-axis deflection input of storage display 133. The X-axis display will be centered on the central electret strip 103 of array 102.

The control counter 140 is stepped through its sequence by a divide-by-N counter 150 which is connected to the output of amplifier 127. Typically, after 5 input cycles from amplifier 127, the control counter 140 can receive one clock pulse from counter 150 to cause multiplexer 130 to select the next strip 103 for display of its output voltage in the storage display 133.

A push-to-start control 151 is connected to counters 140 and 150 to initiate the scanning of the output of the electrets 103. as follows. When the push-to-start control 151 is activated, the divide-by-N counter 150 and the control or select counter 140 are reset to zero and the storage display 133 is erased. The analog multiplexer 130 then connects the first electret transducer 103 to the buffer amplifier 131 and the display generator to display the voltage generated by the first element 103.

The reference signal from amplifier 127 is applied simultaneously to the modulo N counter 150 and control counter 140. After N cycles (typically, N=5) the control counter receives a clock pulse from the modulo N counter 140. The analog multiplexer 130 then selects the next strip transducer 103. Simultaneously the D/A converter 141 drives the X-axis of the storage display 133 to the next position. After this process is repeated 16 times, the modulo N counter 150 is disabled, causing the display to remain until a new measurement is desired. Less than 3 seconds are required to scan all 16 transducers and display the results when f=30 Hz and N=5.

The piezoelectric voltage output of each transducer element is measured as follows: The output of the element selected by the analog multiplexer 130 is buffered by amplifier 131 and then fed to lock-in amplifier 132. The reference signal generated by photocell amplifier 127 is also applied to the lock-in amplifier. The lock-in amplifier generates a d-c signal proportional to the in-phase component of the output of the electret strip 103. This d-c signal drives the Y-axis of the storage display 133. Thus the storage display contains a record of the piezoelectric voltage of each strip 103, which record will be similar to that shown in FIG. 11 if there is an inclusion in the breast tissue lying beneath the array 102.

Although a preferred embodiment of this invention has been described, many variations and modifications will now be apparent to those skilled in the art, and it is therefore preferred that the instant invention be limited not by specific disclosure herein but only by the appended claims.

What is claimed is:

1. An instrument for viscoelastic measurement of human tissue comprising a thin, flat, flexible support sheet; a plurality of spaced transducer elements supported on said support sheet, a planar pressure applying member in surface-to-surface contact with one surface of said support sheet for pressing said spaced transducer elements into a body being examined, means for applying a varying force to said pressure applying member at a given frequency, and circuit means connected to each of said transducer elements for determining a difference in the output of adjacent elements which is indicative of an inclusion in said tissue.

2. The instrument of claim 1 wherein said transducer elements are electrets having a viscoelastic impedance which is close to that of the tissue being examined.

3. The instrument of claim 2 wherein said circuit means includes a storage display means to visually display the output of each of said plurality of transducer elements in a Cartesian coordinate display.

4. The instrument of claim 1 wherein said transducer elements are each thin elongated strips disposed parallel to one another.

5. The instrument of claim 4 wherein said circuit means includes a storage display means to visually display the output of each of said plurality of transducer elements in a Cartesian coordinate display.

6. The instrument of claim 5 which further includes means for applying normal or shear stresses, static or dynamic, or any combination thereof, to the said human tissue.

7. The instrument of claim 1 wherein said circuit means includes a storage display means to visually display the output of each of said plurality of transducer elements in a Cartesian coordinate display.

8. The instrument of claim 1 which further includes means for applying a constant force to said pressure applying member.

* * * * *